US011033868B2

United States Patent
Zhang et al.

(10) Patent No.: US 11,033,868 B2
(45) Date of Patent: Jun. 15, 2021

(54) CONTINUOUS FLOW CATALYTIC REACTOR, ASSEMBLING METHOD THEREFOR AND APPLICATION THEREOF

(71) Applicant: NINGBO INSTITUTE OF MATERIALS TECHNOLOGY & ENGINEERING, CHINESE ACADEMY OF SCIENCE, Ningbo (CN)

(72) Inventors: Yexin Zhang, Ningbo (CN); Jian Zhang, Ningbo (CN); Hui Chen, Ningbo (CN); Jie Yang, Ningbo (CN)

(73) Assignee: NINGBO INSTITUTE OF MATERIALS TECHNOLOGY & ENGINEERING, CHINESE ACADEMY OF SCIENCE, Ningbo (CN)

( * ) Notice: Subject to any disclaimer, the term of this patent is extended or adjusted under 35 U.S.C. 154(b) by 0 days.

(21) Appl. No.: 16/979,532

(22) PCT Filed: Sep. 29, 2018

(86) PCT No.: PCT/CN2018/108703
§ 371 (c)(1),
(2) Date: Sep. 10, 2020

(87) PCT Pub. No.: WO2020/062156
PCT Pub. Date: Apr. 2, 2020

(65) Prior Publication Data
US 2020/0406211 A1 Dec. 31, 2020

(51) Int. Cl.
*B01J 8/00* (2006.01)
*B01J 8/02* (2006.01)
(Continued)

(52) U.S. Cl.
CPC ............. *B01J 8/065* (2013.01); *B01J 8/0015* (2013.01); *B01J 8/0292* (2013.01); *C07H 1/00* (2013.01);
(Continued)

(58) Field of Classification Search
CPC ..... B01J 8/00; B01J 8/0015; B01J 8/02; B01J 8/0292; B01J 8/06; B01J 8/065;
(Continued)

(56) References Cited

FOREIGN PATENT DOCUMENTS

| CN | 101033192 A | 9/2007 |
|---|---|---|
| CN | 204503034 U | 7/2015 |

(Continued)

OTHER PUBLICATIONS

Zhang et al,. MoOx Nanoparticle Catalyst for D-Glucose Epimerization and Their Electrical Immobilization in a Continuous Flow Reactor, Nov. 4, 2019, ACS Appl. Mater. Interfaces 2019, 11, 44118-44123 (Year: 2019).*

(Continued)

*Primary Examiner* — Natasha E Young
(74) *Attorney, Agent, or Firm* — Bayramoglu Law Offices LLC

(57) ABSTRACT

A continuous flow catalytic reactor, an assembling method therefor and an application thereof includes a reaction vessel, a filler packaged in the reaction vessel and a charged catalytic component; the charged catalytic component is fixed to the filler under an action of a direct-current electric field. The continuous flow catalytic reactor may be applied to continuous flow reactions such as a monosaccharide epimerization reaction. A monosaccharide epimerization reaction method includes: providing the continuous flow catalytic reactor; electrically connecting the continuous flow catalytic reactor with a direct-current power supply, thereby to forming the direct-current electric field by electrically (Continued)

connecting the continuous flow catalytic reactor with the direct-current power supply; and heating a reactor container to a target temperature, and inputting a monosaccharide solution from a liquid flow inlet of the reaction vessel and then collecting a solution containing a target product from a liquid flow outlet of the reaction vessel.

15 Claims, 1 Drawing Sheet

(51) Int. Cl.
*B01J 8/06* (2006.01)
*C07H 1/00* (2006.01)
*C07H 3/02* (2006.01)

(52) U.S. Cl.
CPC ....... *C07H 3/02* (2013.01); *B01J 2208/00884* (2013.01); *B01J 2208/026* (2013.01)

(58) Field of Classification Search
CPC .......... B01J 2208/00; B01J 2208/00796; B01J 2208/00884; B01J 2208/02; B01J 2208/023; B01J 2208/024; B01J 2208/026; C07H 1/00; C07H 3/00; C07H 3/02
See application file for complete search history.

(56) References Cited

FOREIGN PATENT DOCUMENTS

| CN | 108452793 A | 8/2018 |
|---|---|---|
| WO | 2011133536 A1 | 10/2011 |

OTHER PUBLICATIONS

Machine translation of CN 108452793 A, which was provided in IDS filed on Sep. 16, 2020 and published on Aug. 28, 2018 (Year: 2018).*

Angela Kockritz et al., Rearrangement of glucose to mannose catalysed by polymer-supported Mo catalysts in the liquid phase, Applied Catalysis A: General, 2008, pp. 112-118, 334.

Ludivine Van Den Biggelaar et al., Enantioselective Transamination in Continuous Flow Mode with Transaminase Immobilized in a Macrocellular Silica Monolith, Catalysts, 2017, pp. 1-13, 7, 54.

Weike Su et al., Development and Application of Continuous-flow Technology in Pharmaceutical "Hazardous Processes", Chinese Journal of Pharmaceuticals, 2017, pp. 469-482, 48(4).

He Tao et al., The Continuous Flow Micro-Reaction, Progress in Chemistry, 2016, pp. 829-838, 28(6).

* cited by examiner

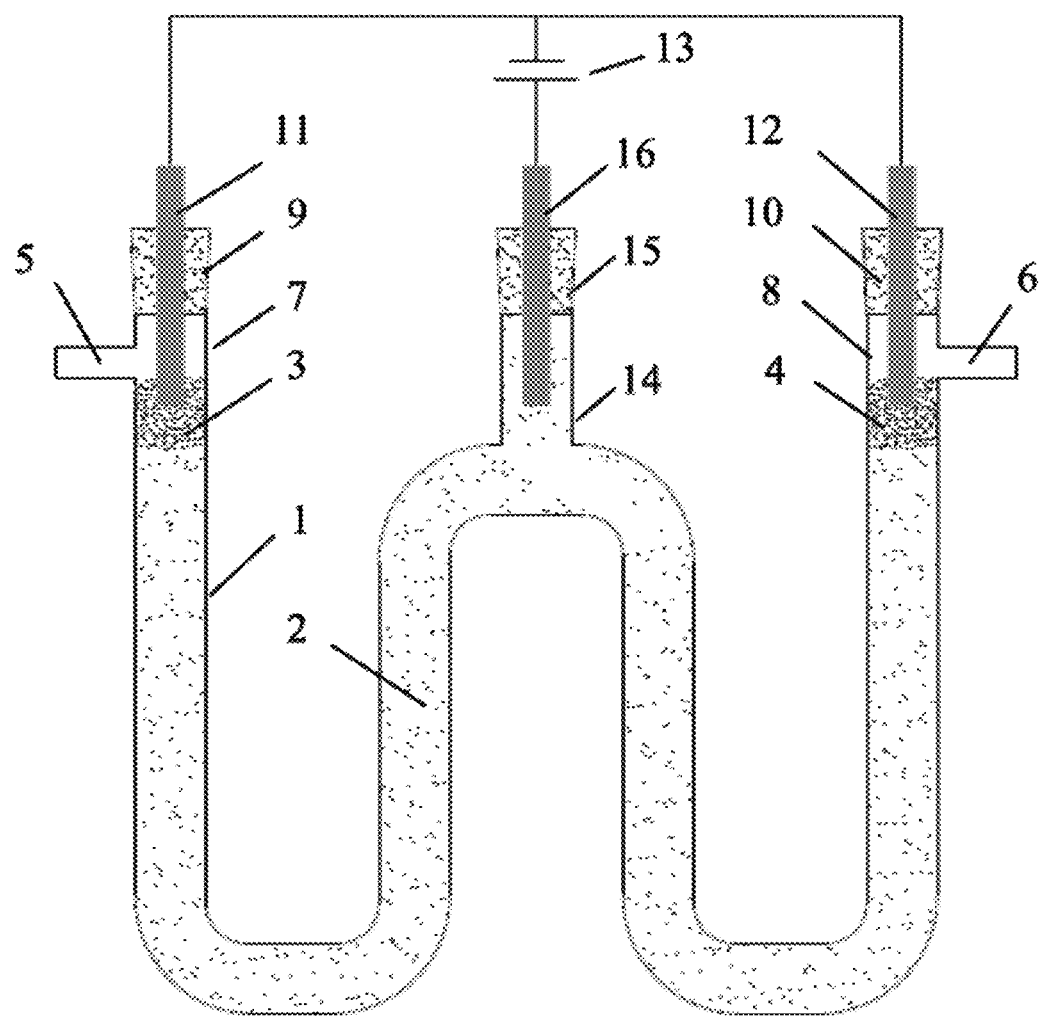

CONTINUOUS FLOW CATALYTIC REACTOR, ASSEMBLING METHOD THEREFOR AND APPLICATION THEREOF

CROSS REFERENCE TO THE RELATED APPLICATIONS

This application is the national stage entry of International Application No. PCT/CN2018/108703, now WO 2020/062156, filed on Sep. 29, 2018, the entire contents of which are incorporated herein by reference.

TECHNICAL FIELD

The disclosure relates to a continuous flow catalytic reactor, an assembling method therefor and application thereof, for example in monosaccharide epimerization reaction.

BACKGROUND

The traditional kettle type liquid phase reaction solves the problem of needs of lots of chemical products, but there are also many defects difficultly overcome by their owns, such as potential safety hazard, environmental pollution, huge energy consumption, unstable product quality, large occupied area and difficult process amplification (Progress in Chemistry, 2016, 28 (6): 829-838). Continuous flow reaction just right solves these problems in views of unique mixing manner, efficient mass and heat transfer and low solvent need. "Continuous flow chemistry" or "Flow chemistry" refers to a technology that materials are delivered through a pump and undergo chemical reaction in a continuous flow manner. In recent 20 years, the continuous flow reaction technology is more and more popular with people in academics and industry, and its advantages are mainly that: (1) the reactor is small in size, rapid in mass and heat transfer, and easily realizes process strengthening: (2) parameter control is precise, reaction selectivity is good, and the technology is especially suitable for inhibiting cascade side reaction; (3) on-line material amount is less, the tiny channel has inherent flame retardant property, the small structure enhances the anti-explosion property of the device, and operation is safe; (4) operation is continuous, and space-time efficiency is high; (5) automatic control is easy to realize, the safety of operation is enhanced, and labor resources are saved (Chinese Journal of pharmaceutical industry, 2017, 48 (4):

Most of liquid phase continuous flow reactions are catalytic reactions, generally, a catalyst is premixed with raw materials and then introduced into a reactor to be reacted. If the catalyst is fixed in the reactor, a catalyst separation step can be saved, so as to reduce the loss of the catalyst, improve the utilization efficiency of the catalyst and prolong the service life of the catalyst. The common catalyst immobilization methods comprise a physical adsorption method and a chemical bonding method. CN101033192A discloses a continuous flow reaction method for producing mononitrobenzene by nitrating benzene with nitric acid, in which metal oxide is loaded to a MFI topology structure molecular sieve and pseudo-boehmite through impregnation way, then pressed and formed into a fixed-bed catalyst; Biggelaar et al. fixed ω-transaminase on porous silicon oxide modified by 3-aminopropyltriethoxy silane via a covalent bond, which was used for continuous flow reaction of enantioselective amino transfer (Catalysts, 2017, 7(2): 54); Köckritz et al. fixed molybdate ions on anion exchange resin by ion bonds to be used for epimerization from glucose to mannose (Applied Catalysis A, 2008, 334 (1-2): 112-118). However, a binding force between a catalytic active component and a supporter is limited, and the former is easily dissolved into liquid medium in continuous flow reaction to cause the lost of the activity of the catalytic active component, thereby resulting in the limited service life of the catalyst.

SUMMARY

The main objective of the present application is to provide a continuous catalytic reactor, an assembling method therefor and application thereof, so as to overcome the defects of the prior art.

In order to realize the foregoing objective of the disclosure, the technical solution adopted by the present application comprises:

The embodiments of the present application provide a continuous flow catalytic reactor, comprising a reaction vessel and a filler packaged in the reaction vessel, wherein the continuous flow catalytic reactor also comprises a charged catalytic component, the catalytic component being fixed to the filler under the action of a direct-current electric field.

The embodiments of the present application provide an assembling method for the continuous flow catalytic reactor, comprising:

putting a filler into a reaction vessel, sealing a liquid flow inlet and a liquid flow outlet of the reaction vessel with a fiber sealing material, the fiber sealing material allowing the liquid flow to pass but block the filler;

electrically connecting the liquid flow inlet and the liquid flow outlet of the reaction vessel with a positive electrode or a negative electrode of the direct-current power supply, and connecting the positive electrode or the negative electrode of the direct-current power supply with the middle part of the filler; and inputting a solution containing the charged catalytic component into the reaction vessel from the liquid flow inlet and then outputting from the liquid flow outlet, thereby fixing the catalytic component on the filler.

The embodiments of the present application also provide application of a continuous flow catalytic reactor in monosaccharide epimerization reaction.

The embodiments of the present application also provide a monosaccharide epimerization reaction method, comprising:

providing the continuous flow catalytic reactor;

electrically connecting the continuous flow catalytic reactor with the direct-current power supply, thereby forming the direct-current electric field; and heating the reaction vessel to a target temperature, and inputting monosaccharide solution from the liquid flow inlet of the reaction vessel and then collecting the solution containing a target product from the liquid flow outlet of the reaction vessel.

Compared with the prior art, the continuous flow catalytic reactor of the present application immobilizes the charged catalytic component on the filler by utilizing the direct-current electric field to constitute a fixed-bed catalyst. The reaction solution is input at the target temperature and reacts under the action of the catalytic component, and then the target product is continuously obtained. In this process, since being fixed by the direct-current electric field, the catalytic component cannot flow out with the product, thereby saving the separation step of the catalyst and promoting the utilization efficiency of the catalyst. Through utilization of the reactor, the molybdenum oxide quantum dots or the molybdate ions are utilized as the catalytic component to realize the continuous reaction of monosaccharide epimerization. In addition, external addition of the direct-current electric field may promote some chemical reactions sensitive to the electric field.

BRIEF DESCRIPTION OF THE DRAWINGS

FIG. 1 is a structural diagram of a continuous flow catalytic reactor according to example 1 of the present application.

DETAILED DESCRIPTION OF THE EMBODIMENTS

In view of the defects in the prior art, the inventor of the present application proposes the technical solution of the present application via long-term research and practice. A more detailed explanation will be given below.

A continuous flow reactor provided by embodiments of the present application comprises a reaction vessel, a filler packaged in the reaction vessel and a charged catalytic component, wherein the catalytic component is fixed to the filler under the action of a direct-current electric field.

In some embodiments, the reaction vessel is of a tubular structure;

In some embodiments, the reaction vessel is made of a glass material, of course, can also be made of other materials, such as ceramics and organic materials.

In some embodiments, the filler comprises any one or a combination of two of activated carbon and ion exchange resin, but is not limited thereto.

In some embodiments, the catalytic component comprises a quantum dot, for example, can be a molybdenum oxide quantum dot.

In some embodiments, the catalytic component comprises a molybdate ion or a ferric hydroxide colloid particle, but is not limited thereto.

In some embodiments, the reaction vessel is 1.5~2 cm in inner diameter, 50~80 cm in length and 100~200 ml in volume;

In some embodiments, the particle size of the filler is 10~50 meshes, and the mass-volume ratio of the total quality of the filler to the volume of the reaction vessel is 50~120 g:100~200 ml.

In some embodiments, the voltage of a direct-current power supply is 5~50 V.

Embodiments of the present application also provide an assembling method for the above-mentioned any continuous flow catalytic reactor, comprising:

putting a filler into a reaction vessel, sealing the liquid flow inlet and the liquid flow outlet of the reaction vessel with the fiber sealing material, the fiber sealing material allowing the liquid flow to pass but block the filler;

electrically connecting the liquid flow inlet and the liquid flow outlet of the reaction vessel with the positive electrode or the negative electrode of the direct-current power supply, and connecting the positive electrode or the negative electrode of the direct-current power supply with the middle part of the filler; and inputting the solution containing the charged catalytic component into the reaction vessel from the liquid flow inlet and then outputting from the liquid flow outlet, thereby fixing the catalytic component on the filler.

In some embodiments, the fiber sealing material comprises glass wool or quartz wool, but is not limited thereto.

In some specific embodiments, the filler can be put into the reactor tube, the two ends of the reaction tube are sealed with glass wool or quartz wool, the middle part of the filler is in short circuit with the positive electrode or the negative electrode of the direct-current power supply, glass wool or quartz wool at the two ends are in short circuit with opposite electrodes. After electrification, a certain volume of aqueous solution containing the catalytic component is pumped in from one end of the reaction tube and then pumped out from the other end.

In some embodiments, the voltage of the direct-current power supply is 5~50 V

In some embodiments, the solution containing the charged catalytic component is quantum dot solution.

In some embodiments, the concentration of the quantum dot solution is 0.5~1 g/l, and flow is 0.2~1 m/min.

In some embodiments, the solution containing the charged catalytic component is a solution containing molybdate ions or ferric hydroxide colloid particles.

Embodiments of the present application also provide application of the above-mentioned any continuous flow catalytic reactor in monosaccharide epimerization reaction.

Embodiments of the present application also provide a monosaccharide epimerization reaction method, comprising:

providing the above-mentioned any continuous flow catalytic reactor;

electrically connecting the continuous flow catalytic reactor with the direct-current power supply, thereby forming the direct-current electric field; and heating the reactor to a target temperature, and inputting monosaccharide solution from the liquid flow inlet of the reaction vessel and then collecting the solution containing the target product from the liquid flow outlet of the reaction vessel.

In some embodiments, the target temperature is 60~120° C.

In some embodiments, the voltage of the direct-current power supply is 5~50 V.

In some embodiments, the monosaccharide solution contains any one or a combination of more of glucose, mannose, arabinose, ribose, xylose and lyxose, but is not limited thereto.

In some embodiments, the concentration of the monosaccharide solution is 1~10 wt %.

In some embodiments, the flow of the monosaccharide solution is 0.1~2 ml/min.

In the continuous flow catalytic reactor provided by the present application, the charged catalytic component is immobilized onto the filler by utilizing the direct-current electric field to constitute the fixed bed catalyst, thereby well inhibiting the charged catalytic component to be lost in the continuous flow reaction.

The continuous flow catalytic reactor of the present application has the advantages of simple structure, unattended operation, safe and convenient operation and the like. The continuous flow catalytic reactor of the present application is utilized to carry out multiple continuous flow reactions, for example, the continuous reaction with monosaccharide epimerization can be realized by taking molybdenum oxide quantum dots or molybdate ions as the catalytic component. In the process of continuous flow reaction, the reaction solution is pumped at the target temperature to react under the action of the catalytic component so as to continuously obtain the target product. Where, because the catalytic component is fixed by the direct-current electric field, it does not flow out with the product, thereby saving the separation steps of the catalyst and improving the utilization efficiency of the catalyst.

The present application will be described in detail in combination with the following drawings and examples. It should be noted that the examples in the present application and the features in the examples can be combined with each other without conflict.

Example 1: the structure of a continuous flow catalytic reactor in this example is as shown in FIG. 1. Where, the reaction tube 1 is W-shaped, made of glass and has an inner diameter of 1.8 cm, a length of 70 cm and a volume of 178 ml. The reaction tube 1 was filled with a coconut shell activated carbon filler 2 with a particle size of 12-30 meshes and a weight of 80 g. Both ends of the filler were respectively sealed with quartz wool 3 and 4; openings 7 and 8 were respectively formed near a liquid inlet 5 and a liquid outlet 6, and graphite electrodes 11 and 12 were sealed and fixed with silica gel plugs 9 and 10; the two electrodes went deep into the reaction tube 1 to be in short circuit with quartz wools 3 and 4 and in short circuit with the negative electrode of a direct-current power supply 13; an opening 14 was formed in the middle of the reaction tube, the graphite electrode 16 was sealed and fixed with a silica gel plug 15, the electrode went deep into the reaction tube 1 to be in short circuit with the filler 2 and to be in short circuit with the positive electrode of the direct-current power supply 13.

200 ml of molybdenum oxide quantum dot solution with a concentration of 0.8 g/l was prepared. The direct-current power supply 13 was turned on, the voltage was kept in 24 V, the solution was pumped into the reaction tube 1 from the liquid inlet at a flow of 0.5 ml/min, flowed through the filler 2 and then was pumped out from the liquid outlet 6, the quantum dots were electrically adsorbed on the filler 2, and the continuous flow reactor was obtained after the solution completely flowed out.

Example 2: a chlorine ion exchange resin filler 2 with a particle size of 20~50 meshes and a weight of 100 g was filled in the reaction tube 1 in example 1, two ends of the filler were sealed with glass wools 3 and 4, and a manner of connecting the glass wools with the direct-current power supply was the same as that in example 1.

400 ml of molybdic acid solution with a concentration of 0.2 g/l was prepared. The direct-current power supply 13 was turned on, the voltage was kept in 10 V, the solution was pumped into the reaction tube 1 from the liquid inlet at a flow of 2 ml/min, flowed through the filler 2 and then was pumped out from the liquid outlet 6, and the molybdic acid ions were electrically adsorbed on the filler 2, so as to obtain the continuous flow reactor.

Example 3: a coconut activated carbon filler 2 with a particle size of 12~30 meshes and a weight of 80 g was filled in the reaction tube 1 in example 1. Two ends of the filler were sealed with glass wools 3 and 4. The connection directions of the positive and negative electrodes of the direct-current power supply were opposite to those in example 1, the glass wools 3 and 4 at the two ends of the filler were in short circuit with the positive electrode of the power supply 13, and the middle of the filler was in short circuit with the negative electrode of the power supply 14.

100 ml of ferric hydroxide sol with a concentration of 0.2 g/l was prepared. The direct-current power supply 13 was turned on, the voltage was kept in 50 V, the sol was pumped into the reaction tube 1 from the liquid inlet at a flow of 0.2 ml/min, flowed through the filler 2 and then was pumped out from the liquid outlet 6, and ferric hydroxide colloid particles were electrically adsorbed on the filler 2, so as to obtain the continuous flow reactor.

Example 4: the reactor in example 1 was heated using water bath, the reaction tube 1 was immersed into a water bath pot, the liquid inlet 5 and the liquid outlet 6 were kept above the water surface, the reactor was heated to 80° C., the direct-current power supply 13 was turned on, and the voltage was kept in 24 V; glucose solution, with a mass concentration of 3% and a flow of 0.3 ml/min, was pumped from the liquid inlet 5; a solution containing target product mannose was collected from the liquid outlet 6. The reaction was continuously carried out for 7 days, and the yield of mannose was kept in about 23%.

Example 5: the reactor in example 1 was heated using oil bath, the reaction tube 1 was immersed into an oil bath pot, the liquid inlet 5 and the liquid outlet 6 were kept above the oil surface, the reactor was heated to 90° C., the direct-current power supply 13 was turned on, and the voltage was kept in 24 V; mannose solution, with a mass concentration of 1% and a flow of 0.1 ml/min, was pumped from the liquid inlet 5; a solution containing target product glucose was collected from the liquid outlet 6. The reaction was continuously carried out for 7 days, and the yield of glucose was kept in about 60%.

Example 6: the reactor in example 2 was heated using oil bath, the reaction tube 1 was immersed into an oil bath pot, the liquid inlet 5 and the liquid outlet 6 were kept above the oil surface, the reactor was heated to 100° C., the direct-current power supply 13 was turned on, and the voltage was kept in 40 V; arabinose solution, with a mass concentration of 5% and a flow of 1 ml/min, was pumped from the liquid inlet 5; a solution containing target product ribose was collected from the liquid outlet 6. The reaction was continuously carried out for 3 days, and the yield of ribose was kept in about 35%.

Example 7: the reactor in example 2 was heated using oil bath, the reaction tube 1 was immersed into an oil bath pot, the liquid inlet 5 and the liquid outlet 6 were kept above the oil surface, the reactor was heated to 100° C., the direct-current power supply 13 was turned on, and the voltage was kept in 40 V; ribose solution, with a mass concentration of 5% and a flow of 1 ml/min, was pumped from the liquid inlet 5; a solution containing target product arabinose was collected from the liquid outlet 6. The reaction was continuously carried out for 3 days, and the yield of arabinose was kept in about 62%.

Example 8: the reactor in example 1 was heated using oil bath, the reaction tube 1 was immersed into an oil bath pot, the liquid inlet 5 and the liquid outlet 6 were kept above the oil surface, the reactor was heated to 110° C., the direct-current power supply 13 was turned on, and the voltage was kept in 10 V; xylose solution, with a mass concentration of 10% and a flow of 2 ml/min, was pumped from the liquid inlet 5; a solution containing target product lyxose was collected from the liquid outlet 6. The reaction was continuously carried out for 3 days, and the yield of lyxose was kept in about 30%.

Example 9: the reactor in example 1 was heated using oil bath, the reaction tube 1 was immersed into an oil bath pot, the liquid inlet 5 and the liquid outlet 6 were kept above the oil surface, the reactor was heated to 120° C., the direct-current power supply 13 was turned on, and the voltage was kept in 10 V; lyxose solution, with a mass concentration of 10% and a flow of 2 ml/min, was pumped from the liquid inlet 5; a solution containing target product xylose was collected from the liquid outlet 6. The reaction was continuously carried out for 3 days, and the yield of xylose was kept in about 52%.

Comparative example 1: 250 g of sodium molybdate was dissolved into water so that the final volume reached a constant volume of 500 ml, 303 g of chlorine ion exchange resin was added, the above raw materials were stirred for 16 h at room temperature, 5 drops of 33% hydrogen peroxide solution was added, a solid was washed with water and filtered for 5 times, 1 mol/l hydrochloric acid was then dropwise added after suction to adjust pH to 3.5, and a wet catalyst was obtained via filtration. The wet catalyst was put into a 25 ml glass tube capable of being electrically heated and having a thermocouple, the fused glass was packaged with glass wool to obtain the continuous flow reactor. The glucose solution (mass concentration was 50%, and pH was adjusted to 3.5 with 2 mol/l hydrochloric acid) was pumped at 90° C. at the flow of 50 m/h to perform epimerization continuous flow reaction. The initial yield of mannose was about 22%. Due to loss of molybdenum, the yield was reduced to 3% after reaction for 3 days. (reference: Applied Catalysis A, 2008, 334 (1-2): 112-118).

Comparative example 2: 44.14 g of molybdenic acid was dissolved into water at 70° C. so that the volume reached a constant volume of 500 ml, 50 g of chlorine ion exchange resin was added, the above raw materials were stirred for 24 h at 40° C., 1 mol/hydrochloric acid was dropwise added to adjust pH to 3.5, then a solid was washed with water and filtered for 5 times to obtain a wet catalyst. The wet catalyst was put into a 25 ml glass tube capable of being electrically heated and having a thermocouple, the fused glass was packaged with glass wool to obtain the continuous flow reactor. The glucose solution (mass concentration was 50%, and pH was adjusted to 3.5 with 1 mol/l hydrochloric acid) was pumped at 90° C. at the flow of 50 ml/h to perform epimerization continuous flow reaction. The initial yield of mannose was about 27%. Due to loss of molybdenum, the yield was reduced to about 23% after reaction for 7 days. The yield was reduced to about 12% after reaction for 33 days, and about ⅓ of molybdenum was lost (reference: Applied Catalysis A, 2008, 334 (1-2): 112-118).

In addition, the inventor of the present application performed tests by using other raw materials, conditions and the like listed in the specification with reference to manners in examples 1-9, and similarly, the continuous flow reactor of the present application is utilized to be successfully applied to continuous flow reaction.

The above examples are only for illustrating the technical conception and features of the present application for the purposes of allowing those skilled in the art to know and implement the contents of the present application, and therefore cannot limit the protective scope of the present application. Equivalent transformations or modifications made according to the spirit of the present application are all included within the protective scope of the present application.

What is claimed is:

1. A continuous flow catalytic reactor, comprising a reaction vessel, a filler packaged in the reaction vessel, and a charged catalytic component, wherein, the charged catalytic component being fixed to the filler under an action of a direct-current electric field.

2. The continuous flow catalytic reactor according to claim 1, wherein the reaction vessel is of a tubular structure; and/or, the reaction vessel is made of a glass material; and/or the filler comprises one of activated carbon and ion exchange resin or a combination of the activated carbon and the ion exchange resin; and/or, the charged catalytic component comprises a quantum dot, wherein the quantum dot comprising a molybdenum oxide quantum dot; or, the charged catalytic component further comprises molybdate ions or ferric hydroxide colloid particles.

3. The continuous flow catalytic reactor according to claim 2, wherein the reaction vessel is 1.5-2 cm in inner diameter, 50-80 cm in length and 100-200 ml in volume; and/or a particle size of the filler is 10-50 meshes, and a mass-volume ratio of a total quality of the filler to the volume of the reaction vessel is 50-120 g:100-200 ml.

4. The continuous flow catalytic reactor according to claim 1, wherein a voltage of a direct-current power supply for forming the direct-current electric field is 5-50 V.

5. An assembling method for the continuous flow catalytic reactor according to claim 1, comprising:
putting the filler into the reaction vessel, sealing a liquid flow inlet and a liquid flow outlet of the reaction vessel with a fiber sealing material, wherein the fiber sealing material allowing liquid flow to pass but blocking the filler;
electrically connecting the liquid flow inlet and the liquid flow outlet of the reaction vessel with a positive electrode or a negative electrode of a direct-current power supply, and connecting the positive electrode or the negative electrode of the direct-current power supply with a middle part of the filler; and
inputting a solution containing the charged catalytic component into the reaction vessel from the liquid flow inlet and then outputting from the liquid flow outlet, and the charged catalytic component is fixed to the filler.

6. The assembling method according to claim 5, wherein the fiber sealing material comprises a glass wool or a quartz wool.

7. The assembling method according to claim 5, wherein a voltage of the direct-current power supply is 5-50 V; and/or, the solution containing the charged catalytic component is a quantum dot solution, and a concentration of the quantum dot solution is 0.5-1 g/l, and a flow is 0.2-1 ml/min; or, the solution containing the charged catalytic component is a solution containing molybdate ions or ferric hydroxide colloid particles.

8. A monosaccharide epimerization reaction method, comprising:
providing the continuous flow catalytic reactor according to claim 1;
electrically connecting the continuous flow catalytic reactor with a direct-current power supply to form the direct-current electric field; and
heating a reactor container to a target temperature, and inputting a monosaccharide solution from a liquid flow inlet of the reaction vessel and then collecting a solution containing a target product from a liquid flow outlet of the reaction vessel.

9. The monosaccharide epimerization reaction method according to claim 8, wherein the target temperature is 60-120° C.; and/or a voltage of the direct-current power supply is 5-50 V; and/or the monosaccharide solution contains any one or a combination of more of glucose, mannose, arabinose, ribose, xylose and lyxose; and/or a concentration of the monosaccharide solution is 1-10 wt %; and/or a flow of the monosaccharide solution is 0.1-2 ml/min.

10. The assembling method for the continuous flow catalytic reactor according to claim 2, comprising:
putting the filler into the reaction vessel, sealing a liquid flow inlet and a liquid flow outlet of the reaction vessel with a fiber sealing material, wherein the fiber sealing material allowing liquid flow to pass but blocking the filler;

electrically connecting the liquid flow inlet and the liquid flow outlet of the reaction vessel with a positive electrode or a negative electrode of a direct-current power supply, and connecting the positive electrode or the negative electrode of the direct-current power supply with a middle part of the filler; and inputting a solution containing the charged catalytic component into the reaction vessel from the liquid flow inlet and then outputting from the liquid flow outlet, and the charged catalytic component is fixed to the filler.

11. The assembling method for the continuous flow catalytic reactor according to claim 3, comprising:

putting the filler into the reaction vessel, sealing a liquid flow inlet and a liquid flow outlet of the reaction vessel with a fiber sealing material, wherein the fiber sealing material allowing liquid flow to pass but blocking the filler;

electrically connecting the liquid flow inlet and the liquid flow outlet of the reaction vessel with a positive electrode or a negative electrode of a direct-current power supply, and connecting the positive electrode or the negative electrode of the direct-current power supply with a middle part of the filler; and inputting a solution containing the charged catalytic component into the reaction vessel from the liquid flow inlet and then outputting from the liquid flow outlet, and the charged catalytic component is fixed to the filler.

12. The assembling method for the continuous flow catalytic reactor according to claim 4, comprising:

putting the filler into the reaction vessel, sealing a liquid flow inlet and a liquid flow outlet of the reaction vessel with a fiber sealing material, wherein the fiber sealing material allowing liquid flow to pass but blocking the filler;

electrically connecting the liquid flow inlet and the liquid flow outlet of the reaction vessel with a positive electrode or a negative electrode of a direct-current power supply, and connecting the positive electrode or the negative electrode of the direct-current power supply with a middle part of the filler; and inputting a solution containing the charged catalytic component into the reaction vessel from the liquid flow inlet and then outputting from the liquid flow outlet, and the charged catalytic component is fixed to the filler.

13. The monosaccharide epimerization reaction method, comprising:

providing the continuous flow catalytic reactor according to claim 2;

electrically connecting the continuous flow catalytic reactor with a direct-current power supply, forming the direct-current electric field by electrically connecting the continuous flow catalytic reactor with the direct-current power supply; and heating a reactor container to a target temperature, and inputting a monosaccharide solution from a liquid flow inlet of the reaction vessel and then collecting a solution containing a target product from a liquid flow outlet of the reaction vessel.

14. The monosaccharide epimerization reaction method, comprising:

providing the continuous flow catalytic reactor according to claim 3;

electrically connecting the continuous flow catalytic reactor with a direct-current power supply, forming the direct-current electric field by electrically connecting the continuous flow catalytic reactor with the direct-current power supply; and heating a reactor container to a target temperature, and inputting a monosaccharide solution from a liquid flow inlet of the reaction vessel and then collecting a solution containing a target product from a liquid flow outlet of the reaction vessel.

15. The monosaccharide epimerization reaction method, comprising:

providing the continuous flow catalytic reactor according to claim 4;

electrically connecting the continuous flow catalytic reactor with a direct-current power supply, forming the direct-current electric field by electrically connecting the continuous flow catalytic reactor with the direct-current power supply; and heating a reactor container to a target temperature, and inputting a monosaccharide solution from a liquid flow inlet of the reaction vessel and then collecting a solution containing a target product from a liquid flow outlet of the reaction vessel.

* * * * *